United States Patent [19]

Bjorkholm

[11] 4,342,914
[45] Aug. 3, 1982

[54] FLYING SPOT SCANNER HAVING ARBITRARILY SHAPED FIELD SIZE

[75] Inventor: Paul J. Bjorkholm, Sharon, Mass.

[73] Assignee: American Science and Engineering, Inc., Cambridge, Mass.

[21] Appl. No.: 191,900

[22] Filed: Sep. 29, 1980

[51] Int. Cl.³ .............................................. H04N 5/32
[52] U.S. Cl. ..................................... 378/99; 358/111; 378/140
[58] Field of Search ............ 250/416 TV, 445 T, 405; 358/111

[56] References Cited

U.S. PATENT DOCUMENTS 2,730,566  1/1956  Bartow et al. ...................... 250/405
4,051,378  9/1977  Krippner ......................... 250/445 T

*Primary Examiner*—Alfred E. Smith
*Assistant Examiner*—T. N. Grigsby

*Attorney, Agent, or Firm*—Pollock, Vande Sande & Priddy

[57] ABSTRACT

A flying spot X-ray scanning system includes a grid controlled X-ray tube and associated collimators for producing a pencil beam of X-rays which is adapted to repeatedly scan along a line through a body to be examined and across an associated detector. The grid of the X-ray tube is energized by a train of rectangularly shaped pulses, and separate control means are provided for selectively varying the commencement of each such pulse thereby to determine the position of the scan field relative to the body being examined, and for selectively varying the duration of each pulse thereby to control the width of the scan field. The X-ray tube, collimators, and detector are adapted to be moved as a unit in a direction transverse to the scan line of the pencil beam, and a further control is provided for selectively varying the extent of this transverse movement thereby to control the longitudinal dimension of the scan field.

16 Claims, 4 Drawing Figures

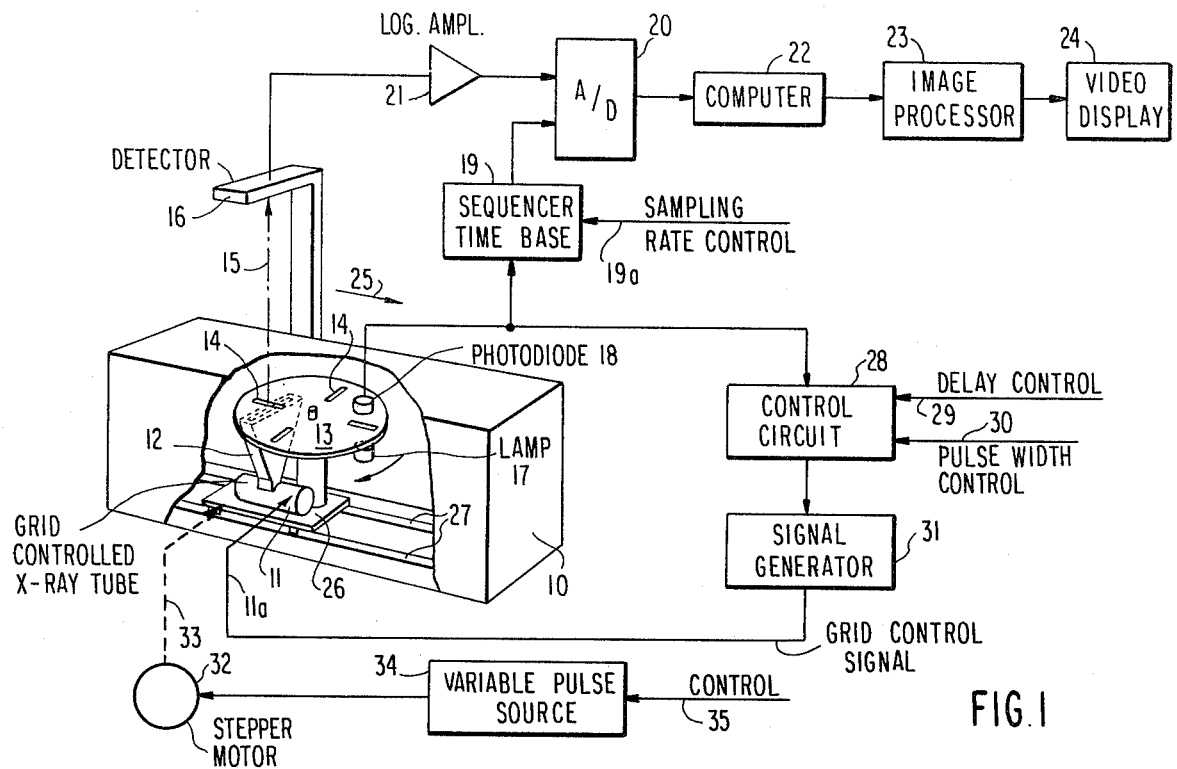
FIG. 1
FIG. 2
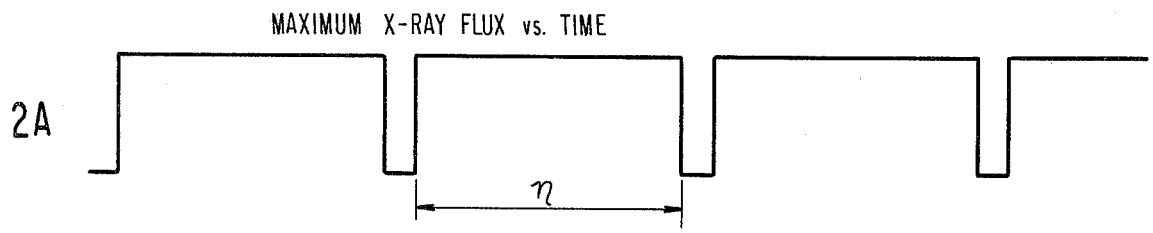
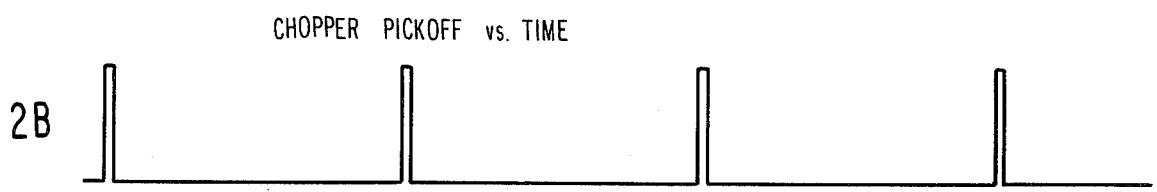
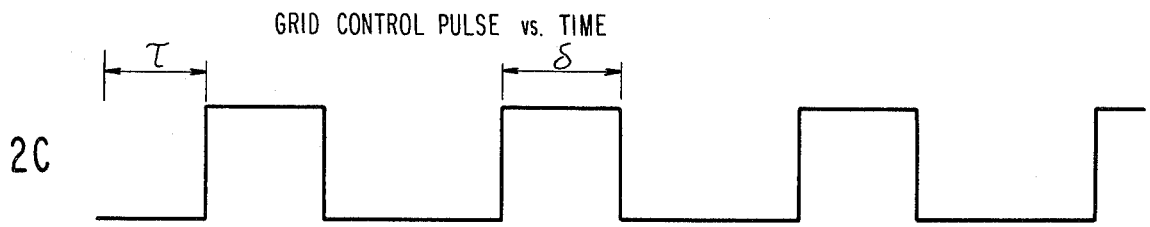

FLYING SPOT SCANNER HAVING ARBITRARILY SHAPED FIELD SIZE

BACKGROUND OF THE INVENTION

Several diagnostic X-ray imaging techniques have been developed in recent years which are variously called digital radiography, electronic radiography, computed radiography and digital fluoroscopy. These systems all have the common element of producing projection radiographic images in a digital form. Some of the advantages proposed for these systems are highly efficient use of dose, scatter reduction, ease of operation, noiseless data transmission, new types of image storage, flexible display capability to exploit the total range of detected information, and a potential for various forms of image manipulation such as edge enhancement, filtering, and subtraction.

One such system which achieves these advantages, and which is accordingly useful as a diagnostic modality over analog radiography systems suggested heretofore, is manufactured by American Science and Engineering, Inc., Cambridge, Mass., and is known as the Micro-Dose ® system. This particular system employs, inter alia, the concept of utilizing a flying spot of X-rays to generate an image. The mechanism employed for this purpose is described generally in Stein et al U.S. Pat. No. 3,780,291 issued Dec. 18, 1973, for "Radiant Energy Imaging With Scanning Pencil Beam", reissued Sept. 2, 1975, as U.S. Pat. No. Re. 28,544, and the overall system when employed for medical diagnostic purposes is described in greater detail in the article "Digital Radiography" by P. J. Bjorkholm, M. Annis, and E. E. Frederick, Proceedings of the Society of Photo-Optical Instrumentation Engineers, *Application of Optical Instrumentation in Medicine VIII*, 137 (1980). In this system, the X-ray beam is shaped and positioned by mechanical collimators. More particularly, the output of a standard rotating anode X-ray tube is collimated to form a narrow fan beam of X-rays, and that fan beam is in turn intercepted by a lead-filled chopper disc having radial slits therein which are so positioned that one and only one slit always intersects the plane of the fan beam. This arrangement allows a small nearly rectangular X-ray pencil beam to pass through the disc to the subject, and causes the pencil beam to be scanned along a line as the chopper disc is rotated. The X-rays transmitted by the subject are detected by a solid state scintillator viewed by a photo tube. The output of the detector as a function of time is correlated with the chopper disc's rotational position to give the X-ray transmission as a function of position within the X-ray plane thereby to generate a one-dimensional cut through the subject. To generate the second dimension, the X-ray tube, collimator, chopper disc, and detector are translated as a unit with respect to the patient. The detector output is then digitized and sent to a computer for storage, manipulation and image creation. A single image consisting of a 512×480 pixel matrix is taken in about 16 seconds.

High contrast resolution, high throughput flying spot scanning systems of the type described above, and of other types to which the present invention is generally applicable, are often flux limited. Also, digital systems can be limited in spatial resolution by the number of pixels available. Both of these considerations suggest that the area scanned be as closely matched to the area of interest as possible. The system described above is capable of achieving this result only in a limited fashion and, more particularly, is so arranged that the equipment can produce field sizes of any one of three different predetermined dimensions, i.e., a large field of 15 by 20 inches, a medium field of 6 by 8 inches, and a small field of 1½ by 2 inches. To achieve these different field sizes, the chopper disc is provided with three different sets of slits, and the chopper disc is physically moved with respect to the slit of the fan beam collimator to select that particular set of radial slits which will achieve the desired one of the field widths mentioned, while, concurrently therewith, the translational speed of the X-ray generating system and associated detector is changed to a selected one of three preset translational speeds which are factory set and which will produce the length of scan field which is preassociated with the selected scan field width during the fixed time of scanning. In short, the field size is determined laterally by the chopper wheel and fan beam geometry, and longitudinally by the translational speed of the source during the scan, but the system is so arranged that only one of three different predetermined field sizes can be selected, with the lengths and widths of these various field sizes always being in the same ratio. The position of any selected field is always fixed relative to the patient being examined and cannot be varied by manipulation of the flying spot X-ray scanning system.

Inasmuch as the dose to the patient is proportional to the area scanned, and inasmuch further as there are some radiological procedures where the area of interest is less than the normal field size and the images could be improved by increased dose, it is highly desirable to provide a system which is adapted to achieve a scan field wherein the length and width of the field can be selectively varied independently on one another, and wherein, moreover, the position of the scan field can be varied relative to the patient by controls on the equipment itself, thereby to make it possible to achieve an arbitrarily shaped and positioned field which is closely matched to the real area of interest. The ability to produce any sized rectangular field represents a considerable improvement in convenience and utility over systems suggested heretofore, and allows maximum utilization of X-ray flux and spatial resolution potential of any given digital system. The present invention is capable of achieving these highly desirable results.

SUMMARY OF THE INVENTION

The present invention will be described by reference to the American Science and Engineering Micro-Dose ® system referred to earlier but, as will be appreciated by those skilled in the art, has application to other types of flying spot X-ray scanning systems.

In general, the system comprises X-ray generating means located adjacent to one side of a region in which a body is to be examined, and detector means located adjacent to the other side of said region, with the X-ray generating means being arranged to produce a pencil beam of X-rays which is adapted to repeatedly scan along a line through said region and across the detector means. Translation means are also provided for effecting relative motion between the X-ray generating means and the body to be examined in a direction transverse to the scan line during the repeated scans, whereby the overall system produces a rectangular X-ray scan field which has one dimension defined by the scanning of the pencil beam along said line, and a transverse dimension defined by the translation means.

In accordance with the improvement of the present invention, the X-ray generating means comprises a grid controlled X-ray tube. Signal generating means are coupled to the grid of the X-ray tube for providing a signal, preferably in the form of a train of spaced rectangular pulses, which controls the emission of X-rays from the tube. First control means are provided for selectively varying the time, during the pencil beam scan, at which each grid control pulse rises to a potential level capable of effecting emission of X-rays from the grid controlled tube thereby to control the position of the scan field relative to the patient being examined; and a second control is provided for selectively varying the duration of each grid control pulse thereby to arbitrarily control the width of the scan field.

A third control, independent of the said first and second controls, is also provided for selectively varying the speed of translation of the pencil beam forming device and its associated detector relative to the patient being examined, thereby to achieve an arbitrary variation in the longitudinal dimension of the field. This third control may comprise a stepping motor which drives a lead screw shaft that is associated with the beam forming device, and a pulse source for energizing the stepping motor and so arranged that the operator can vary the frequency of said source, and therefore the total number of pulses which are supplied to the stepping motor during a predetermined time interval, thereby to achieve any desired field length.

BRIEF DESCRIPTION OF THE DRAWINGS

The foregoing objects, advantages, construction and operation of the present invention will become more readily apparent from the following description and accompanying drawings wherein:

FIG. 1 is a schematic and block diagram illustrating the preferred embodiment of the present invention; and FIG. 2 comprises a series of wave forms 2A, 2B and 2C which show the operation of portions of the system shown in FIG. 1.

DESCRIPTION OF THE PREFERRED EMBODIMENTS

As shown in FIG. 1, a Micro-Dose ® system of the general type described earlier comprises a table 10 on which a patient to be examined may rest. The table 10 houses an X-ray pencil beam generating system comprising an X-ray tube 11 which is adapted to emit radiation, a collimator 12 which is adapted to shape the emitted radiation into a fan beam that emerges through a comparatively narrow slit at the top of collimator 12, and a chopper disc 13 which has a plurality of radial slits or jaws 14 therein. Chopper disc 13 is so positioned relative to collimator 12 that one and only one of the slits 14 always intersects the plane of the fan beam emerging from collimator 12 whereby, as chopper disc 13 rotates, a pencil beam of X-rays 15 having a substantially rectangular cross section emerges from disc 13, passes upwardly through the region in which a body is to be examined on table 10, and scans along a line which is colinear with an elongated detector 16 that is positioned above table 10. The X-rays transmitted by the subject being examined are detected by a solid state scintillator crystal in detector 16, and viewed by an associated photo tube, the crystal being large enough to intercept the whole plane of X-rays formed by collimator 12 independent of the rotational position of the chopper disc 13. At any position of the chopper disc 13, the instrument can measure the transmission of the subject at one point and, to measure an adjacent point, all that is required is that the disc rotate slightly. In practice, the disc rotates at about 1800 rpm.

An independent optical system comprising a lamp 17 positioned below disc 13 and a photo diode 18 positioned above the disc 13 is provided to determine the rotational position of disc 13 as a function of time. Elements 17, 18 are disposed along the path of movement of the several slits 14, and the lamp 17 is comparatively small and its output collimated so that it can be seen by photo diode 18 only at a very small portion of the rotational travel of each slit 14, just slightly before the slit 14 becomes operative as an X-ray collimator. This independent optical system forms a portion of the prior system already described and, in practice, produces a train of comparatively narrow pulses (FIG. 2B), well defined in time, which are used to synchronize data taking.

More particularly, in the aforementioned prior system, the pulses which appear at the output of photodiode 18 are supplied to a sequencer time base circuit 17 whose output is supplied to an analog to digital converter 20. An analog signal is also supplied to said converter 20 from the output of detector 16 via a logarithmic amplifier 21. The pulse output from circuit 19 (FIG. 2B) samples the detector output at the A/D converter 20 to provide digital signals which are sent to a computer 22 for storage and manipulation, and an image is then created by an image processor 23 and video display 24.

The scanning of pencil beam 15 generates a one-dimensional cut through the subject being examined. To generate the second dimension, X-ray tube 11, collimator 12, chopper disc 13, and detector 16 are translated with respect to the patient in a direction 25 transverse to the direction of the pencil beam scan. This is accomplished by mounting the X-ray generating and detector unit on a support structure 26 which is adapted to be translated along tracks 27 within table 10 by an appropriate drive motor. As a result of this arrangement, a two-dimensional image is ultimately produced on video display 24, consisting for example of a 512×480 pixel matrix which is taken in about 16 seconds.

In the prior arrangement described previously, X-ray tube 11 is a standard rotating anode X-ray tube, and produces an X-ray intensity as a function of time above the top of table 10 such as is shown in FIG. 2A, where the high intensity periods of length $\eta$ occur when one of the slits 14 is transversing the slit in collimator 12, and the intervening low intensity periods occur between slits 14. In accordance with the improvement of the present invention, however, tube 11 comprises a grid controlled X-ray tube of known commercial type whose emission can be controlled by a signal supplied to the grid line 11a thereof. If this signal were high all the time, the resultant X-ray intensity above the table top would again correspond to that shown in FIG. 2A, but in accordance with the improvement of the present invention the signal supplied to line 11a is adapted to be selectively varied by the operator of the equipment thereby to control the position of the X-ray scan field and its width.

More particularly, by using the chopper pickoff signals shown in FIG. 2B to synchronize the generation of the grid control signals supplied to line 11a, and by creating a grid control signal of the type shown in FIG. 2C, the position of the X-ray field with respect to the top of table 10 is determined by the time delay τ. The width of the X-ray field is, moreover, controlled by the pulse width or duration δ. The only requirement is that τ+δ is less than or equal to η.

The foregoing is accomplished in the present invention by feeding the chopper pickoff signal from optical system 17, 18 to a control circuit 28 which has two independent control inputs, i.e., a delay control 29 used to select the time delay τ, and a pulse width control input 30 which is used to select the pulse width δ. The chopper pickoff signals trigger the operation of a signal generator 31 under the control of circuit 28 to produce a train of substantially rectangular pulses, (FIG. 2C) each of which commences at a selected delay time subsequent to a given chopper pickoff pulse and each of which has a selected duration thereafter, and this train of pulses is then coupled from signal generator 31 to grid line 11a of grid controlled X-ray tube 11 to define the position and width of the X-ray scan field at the top of table 10.

To achieve a variation in field size along the longitudinal direction, the speed of translation of the beam forming device must be changed. This can be effected in various ways. By way of example, and as shown in FIG. 1, the drive system may include a stepper motor 32 which is coupled as at 33 to a lead screw shaft associated with support 26, and stepper motor 32 is in turn energized from a variable pulse source 34 the frequency of which can be selectively varied by a further control 35. Variation of the frequency and total number of pulses which are supplied to the stepping motor can be used to achieve any length field.

To make optimal use of the arbitrarily shaped field size, the sampling rate should preferably be changed appropriately to match the field size, and the present invention accordingly provides the sequencer time base circuit 19 with a sampling rate control 19a to permit such change. If a single image consists for example of a matrix which is 512 pixels wide, and the width of the scan field is reduced, the sampling rate should be increased to provide 512 pixels within the reduced field width; and, conversely, as the width of the field is increased, the sampling rate should be reduced. Similarly, as the length of the field is increased the sampling rate should be reduced, and as the length of the field is reduced the sampling rate should be increased, to maintain a constant number of pixels in the length direction of the pixel matrix. The sampling rate control 19a is preferably interlocked to the field width control 30 and to the field length control 35 so that the sampling rate is changed automatically and in appropriate fashion with changes in the field size.

Under some circumstances, it may also be desirable to effect changes in the sizes of the slits 14 in chopper disc 13 with changes in field size, although this particular modification of the invention is optional. More particularly, those skilled in the art will understand that if 512 samples are obtained, for example, over a given field width and with a certain slit size, a certain resolution will be achieved; and if the width of the field should then be reduced while still taking the same number of samples and maintaining the same slit size, the resolution which will be achieved in the new video image will be the same as that achieved in the original image, but considerably more flux will be provided to produce the video image. This is a highly desirable result, and represents one of the advantages of the present invention. In other cases, however, it may be desirable to achieve a spatial resolution which changes appropriately with changes in field size, and this can be accomplished by varying the sizes of the slits 14 with variations in field size so that when the field size is reduced the size of slits 14 is also reduced, and vice versa. Such a variation in slit size can be accomplished, for example, by fabricating chopper disc 13 in the form of two superposed discs which are coaxial with one another and each of which is provided with its own set of slits so that the effective slit size which is produced by the composite superposed discs is a function of the slits in both discs and can be varied by incrementally shifting the rotational position of one disc relative to the other.

While I have thus described preferred embodiments of the present invention, many variations will be apparent to those skilled in the art. It must therefore be understood that the foregoing description is intended to be illustrative only and not limitative of the present invention, and all such variations and modifications as are in accord with the principles described are meant to fall within the scope of the appended claims.

Having thus described my invention, I claim:

1. In a flying spot X-ray scanning system of the type comprising means defining a region in which a body to be examined by X-rays may be located, detector means located adjacent one side of said region, X-ray generating means located adjacent the other side of said region for producing a pencil beam of X-rays which is adapted to repeatedly scan along a line through said region and across said detector means, and translation means for effecting relative motion between said X-ray generating means and the body to be examined in a direction transverse to said line during said repeated scans thereby to produce a rectangular X-ray scan field which has one dimension defined by the said scanning of said pencil beam along said line and a transverse dimension defined by said translation means, the improvement wherein said X-ray generating means comprises a grid-controlled X-ray tube, signal generating means coupled to the grid of said X-ray tube for providing a signal which controls the emission of X-rays from said tube, and control means coupled to said signal generating means for selectively varying the time at which said signal commences thereby to control the position of said X-ray scan field relative to said region.

2. The scanning system of claim 1 including second control means coupled to said signal generating means for selectively varying the duration of said signal subsequent to commencement of said signal thereby to control the width of said X-ray scan field.

3. The scanning system of claim 2 wherein third control means are provided for selectively varying the speed of operation of said translation means independently of said first and second control means, thereby to control the length of said X-ray scan field independently of the position and width of said scan field.

4. The scanning system of claim 3 wherein said translation means comprises a stepper motor for moving said X-ray generating means and said detector means relative to the body to be examined, said third control means comprising a variable pulse source coupled to said stepper motor for energizing said motor.

5. The scanning system of claim 3 including sampling means for regularly sampling the output signal produced by said detector means, and means for selectively varying the sampling rate of said sampling means to permit said sampling rate to be changed with changes in the size of said X-ray scan field.

6. The scanning system of claim 2 wherein said X-ray generating means comprises a collimator disposed adjacent said X-ray tube for collimating a beam of X-rays emitted by said tube into a fan beam, a chopper disc mounted for rotation through said fan beam and having a plurality of spaced apertures each of which is operative to produce a pencil beam of X-rays, sensing means responsive to rotation of said disc for generating a train of electrical pulses indicative of the rotational phase of said chopper disc, and means responsive to said electrical pulses for controlling the operation of each of said control means.

7. The scanning system of claim 6 wherein said sensing means comprises a light source disposed adjacent one side of said chopper disc, and light detector means disposed adjacent the other side of said disc and responsive to light passing from said source through said apertures for producing said electrical pulses.

8. The scanning system of claim 1 including means for producing an electrical pulse each time said X-ray generating system is adapted to direct said pencil beam toward the beginning of said line, said control means comprising variable time delay means responsive to said electrical pulse for controlling the time at which emission of said pencil beam commences relative to the beginning of said line.

9. A flying spot X-ray scanning system comprising an X-ray source adapted to emit X-rays, collimator means positioned to intercept said emitted X-rays and operative to produce a pencil beam of X-rays which repetitively scans along a first line, means for moving said X-ray source and said collimator means along a second line transverse to said first line during the scanning of said pencil beam, first control means for selectively varying the time at which said X-ray source commences its emission of X-rays relative to the beginning of each of said scans, second control means for selectively varying the duration of said emission of X-rays subsequent to the commencement of said emission, and third control means for selectively varying the extent to which said X-ray source and collimator means are moved along said second line, whereby said first, second and third control means jointly define the position and dimensions of the X-ray scan field which is generated by said flying spot scanning system.

10. The scanning system of claim 9 wherein said first, second and third control means are operative independently of one another thereby to permit the position and dimensions of said X-ray scan field to be varied arbitrarily.

11. The scanning system of claim 9 wherein said X-ray source comprises a grid-controlled X-ray tube, grid control means for supplying a variable control potential to the grid of said tube, said control potential being adapted to increase in magnitude between a first level operative to suppress the emission of X-rays from said tube and a second level operative to effect the emission of X-rays from said tube, said first control means comprising means operative to switch said control potential from said first level to said second level, and said second control means comprising means operative to switch said control potential from said second level to said first level.

12. The scanning system of claim 11 wherein said grid control means comprises a pulse generator operative to generate a train of spaced substantially rectangular pulses, said first control means being operative to control the commencement of each of said pulses relative to a predetermined datum, and said second control means being operative to control the width of each of said pulses.

13. In a flying spot X-ray scanning system of the type comprising means defining a region in which a body to be examined by X-rays may be located, detector means located adjacent one side of said region, X-ray generating means located adjacent the other side of said region for producing a pencil beam of X-rays which is adapted to repeatedly scan along a line through said region and across said detector means, and translation means for effecting relative motion between said X-ray generating means and the body to be examined in a direction transverse to said line during said repeated scans thereby to produce a rectangular X-ray scan field which has one dimension defined by the said scanning of said pencil beam along said line and a transverse dimension defined by said translation means, the improvement wherein said X-ray generating means comprising a grid-controlled X-ray tube, signal generating means coupled to the grid of said X-ray tube for providing a signal which controls the emission of X-rays from said tube, and control means coupled to said signal generating means for selectively varying the duration of said signal thereby to control the width of said X-ray scan field.

14. The scanning system of claim 13 including further control means coupled to said translation means for selectively varying the length of said X-ray scan field independently of the width of said field.

15. The scanning system of claim 13 wherein said X-ray generating means comprises a grid-controlled X-ray tube, said control means comprising means for supplying grid control pulses of selectively variable duration to the control grid of said tube.

16. The scanning system of claim 15 wherein said X-ray generating means includes a rotating collimator operative to produce said scanning pencil beam, and means responsive to the rotational position of said collimator for synchronizing the times of occurrence of said grid-control pulses.

* * * * *